United States Patent

Sato et al.

[11] Patent Number: 5,779,686
[45] Date of Patent: Jul. 14, 1998

[54] DISPOSABLE MEDICAL INSTRUMENT

[75] Inventors: Yukio Sato, Kodaira; Yutaka Yanuma, Hachioji; Kazuhiko Ohzeki, Hino; Ryuta Sekine, Choufu; Yasuo Miyano, Hachioji, all of Japan

[73] Assignee: Olympus Optical Co., Ltd., Tokyo, Japan

[21] Appl. No.: 718,016

[22] Filed: Sep. 3, 1996

Related U.S. Application Data

[63] Continuation of Ser. No. 530,422, Sep. 18, 1995, abandoned, which is a continuation of Ser. No. 179,944, Jan. 11, 1994, abandoned.

[30] Foreign Application Priority Data

Apr. 19, 1993 [JP] Japan .................. 5-091516
Oct. 22, 1993 [JP] Japan .................. 5-265207

[51] Int. Cl.[6] ............................................. A61B 10/00
[52] U.S. Cl. ............................................ 604/265; 604/110
[58] Field of Search .................................. 604/110, 111, 604/265; 128/749, 753, 754, 756, 751

[56] References Cited

U.S. PATENT DOCUMENTS

| 3,736,939 | 6/1973 | Taylor | 604/265 |
|---|---|---|---|
| 3,861,396 | 1/1975 | Vaillancourt et al. | 604/265 X |
| 3,874,383 | 4/1975 | Glowacki et al. | 604/110 |
| 4,452,776 | 6/1984 | Refojo | 523/111 X |
| 4,781,683 | 11/1988 | Wozniak et al. | 604/110 |
| 4,890,610 | 1/1990 | Kirwan, Sr. et al. | |
| 4,936,835 | 6/1990 | Haaga | 604/265 |
| 4,952,206 | 8/1990 | Ibanez et al. | 604/110 |
| 4,976,693 | 12/1990 | Haast | 604/110 |
| 4,976,704 | 12/1990 | McLees | 604/110 X |
| 4,982,727 | 1/1991 | Sato | 128/4 |
| 5,129,889 | 7/1992 | Hahn et al. | 604/265 |
| 5,254,105 | 10/1993 | Haaga | 604/265 |

*Primary Examiner*—Sam Rimell
*Attorney, Agent, or Firm*—Armstrong, Westerman, Hattori, McLeland & Naughton

[57] ABSTRACT

A disposable medical instrument wherein at least part of the portion which does not directly contact the mucosa in body cavities is composed of a material containing hydrophilic polymer such as water soluble polymer or water absorptive polymer.

12 Claims, 8 Drawing Sheets

5,779,686

1

DISPOSABLE MEDICAL INSTRUMENT

This application is a Continuation of Ser. No. 08/530,422 filed Sep. 18, 1995, now abandoned, which is a continuation of Ser. No. 08/179,944 filed Jan. 11, 1994, now abandoned.

BACKGROUND OF THE INVENTION

1. Field of the Invention

The present invention relates to a disposable medical instrument which is disposed after use.

2. Related Art Statement

Recently, medical instruments which are disposed after use have been employed in medicine, precluding repeated use by washing and disinfecting.

For example, in clamp devices, a treatment section is provided at the front end of a narrow, long sheath, and at the rear end of the sheath, an operating section for operating the treatment section is provided. An advancing/retracting member such as an operating wire the front end of which is connected to the treatment section is inserted through the sheath and the operating section has a slider to which the rear end of the advancing/retracting member is connected. By advancing or retracting the slider, the advancing/retracting member is pushed and pulled respectively to operate the treatment section.

In disposable type medical instruments, the clamp device, for example, includes an operating section composed of cheap plastic because of the one-time use.

Generally, disposable medical instruments which prohibit reuse are thrown away after use.

However, because ordinary disposable instruments can be reused by washing, some operators may use the same instrument repeatedly. If a disposable medical instrument is used repeatedly, its performance which is gauged for single use may deteriorate and trouble may occur.

OBJECTS AND SUMMARY OF THE INVENTION

An object of the present invention is to provide a disposable medical instrument which cannot be reused if it is washed after use, or which makes it possible to judge whether the medical instrument has been washed thereby precluding reuse.

Another object of the present invention is to provide a disposable medical instrument which cannot be reused because a part of the components dissolves in water or expands if it is washed thereby precluding reuse.

Accordingly, there is provided a disposable medical instrument wherein at least part of the portion which does not directly contact the mucosa in body cavities is composed of a material containing hydrophilic polymer.

The other features and advantages of the present invention will be made evident in the following description.

BRIEF DESCRIPTION OF THE DRAWINGS

FIG. 2 is a perspective view showing the components of the front end of the operating section of a treatment instrument.

FIG. 3 is a sectional view showing the components of the front end of the operating section of a treatment instrument.

2

Figure 3:
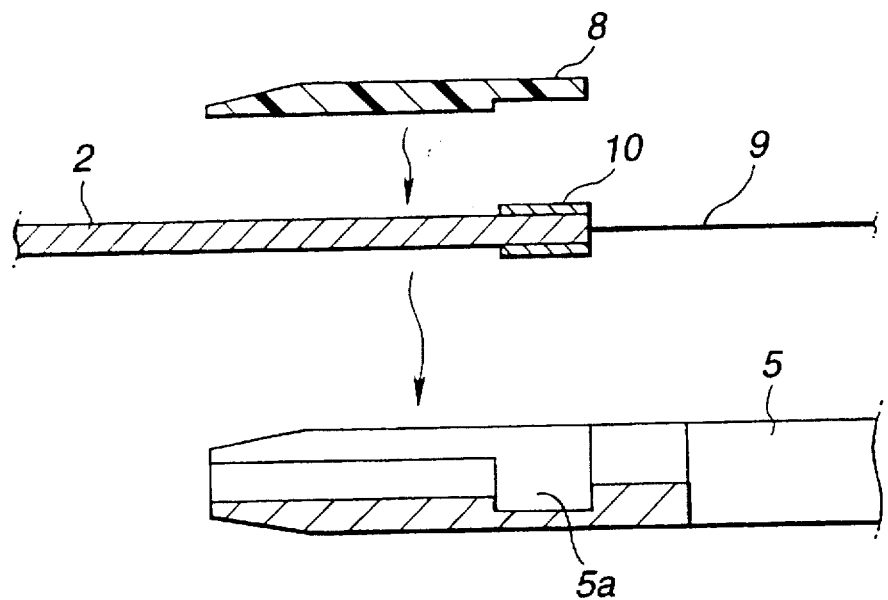
Figure 4:
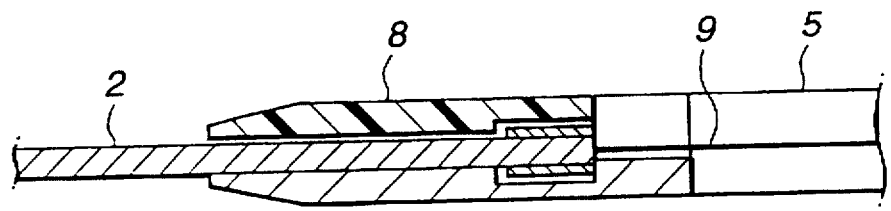

FIG. 4 is a sectional view showing the assembled components of the front end of the operating section shown in FIG. 3.

Figure 5:
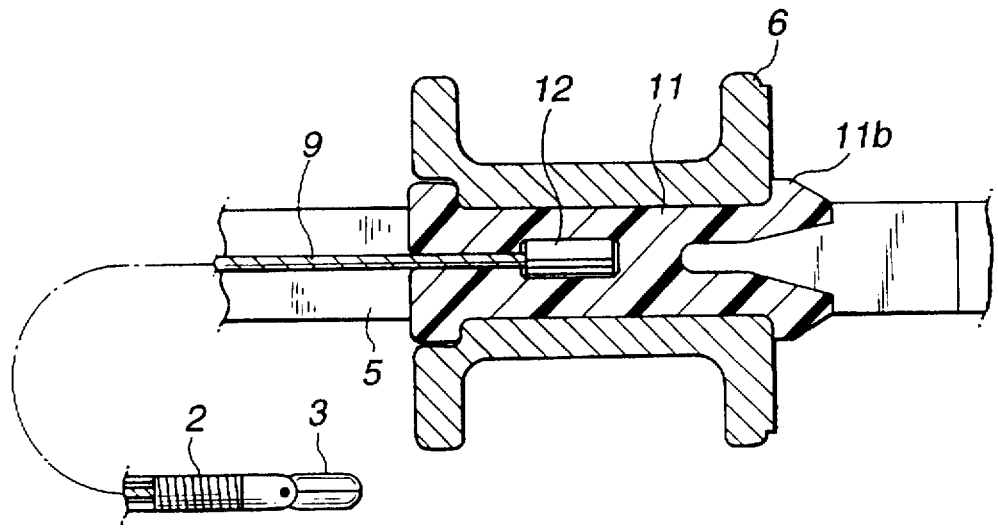

FIG. 5 is a sectional view showing the construction near a slider which is mounted in the center of the operating section of a treatment instrument.

Figure 6:
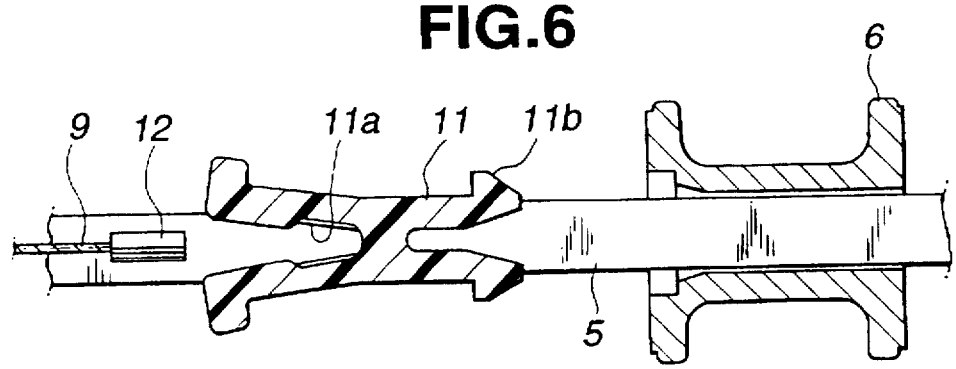

FIG. 6 is a sectional view showing the assembled slider, advancing/retracting member and pressing plate shown in FIG. 5.

Figure 7:
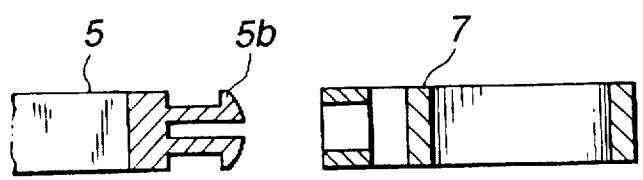

FIG. 7 is a sectional view showing the components of the rear end of the operating section of a treatment instrument.

Figure 8:
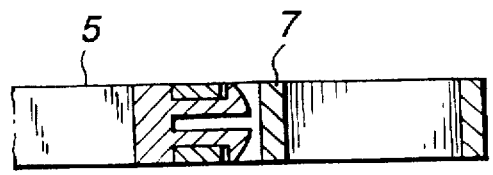

FIG. 8 is sectional view showing the assembled components of the rear end of the operating section shown in FIG. 7.

Figure 9:
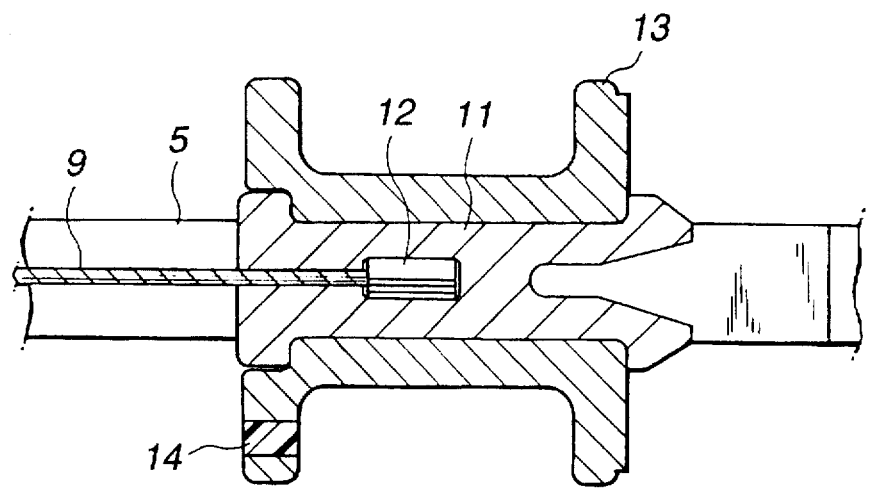

FIG. 9 is a sectional view showing the construction of a slider which is mounted in the center of the operating section of the treatment instrument shown in FIG. 7.

Figure 10:
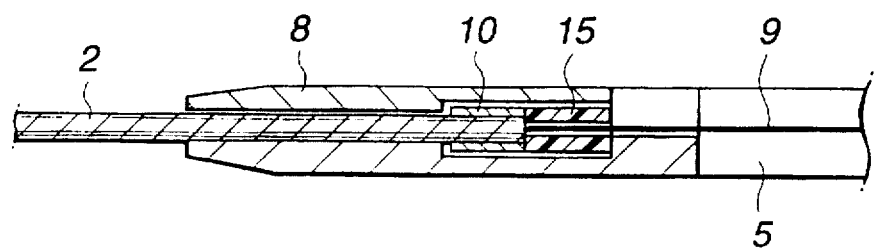
Figure 11:
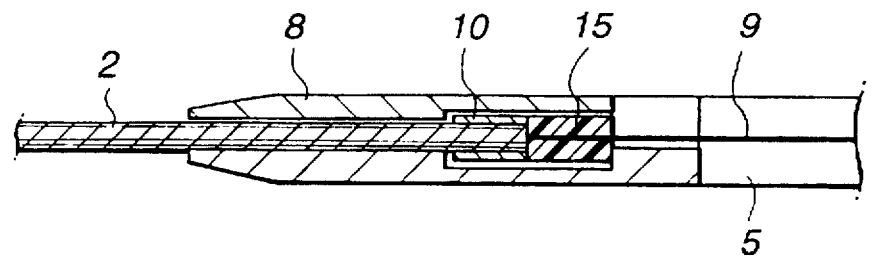

FIGS. 10 and 11 are related to the eighth embodiment of the present invention and FIG. 10 is a sectional view showing the components of the front end of the operating section of a treatment instrument.

FIG. 11 is a sectional view showing the condition in which the hydrophilic ring shown in FIG. 10 is expanded.

Figure 12:
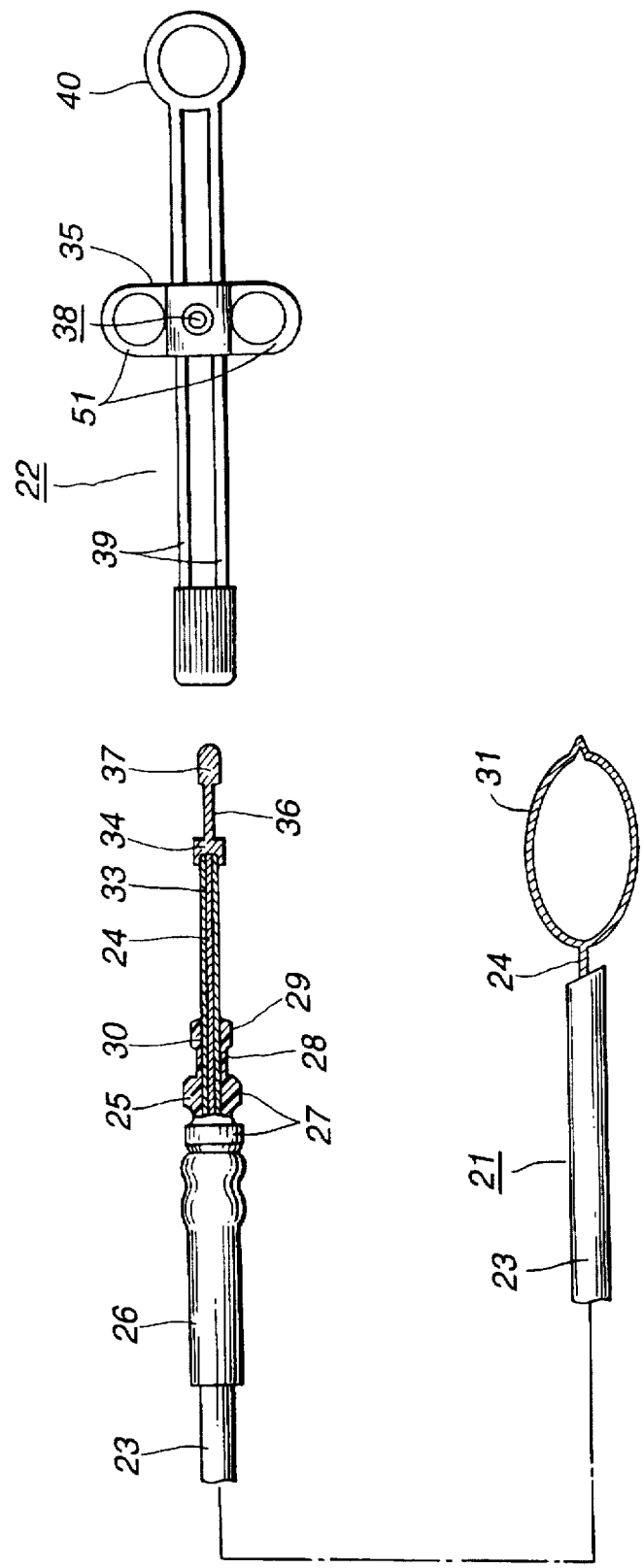

FIGS. 12–18 are related to the ninth embodiment of the present invention and FIG. 12 is an explanatory drawing showing the entire construction of a treatment instrument which is a disposable medical instrument.

Figure 13:
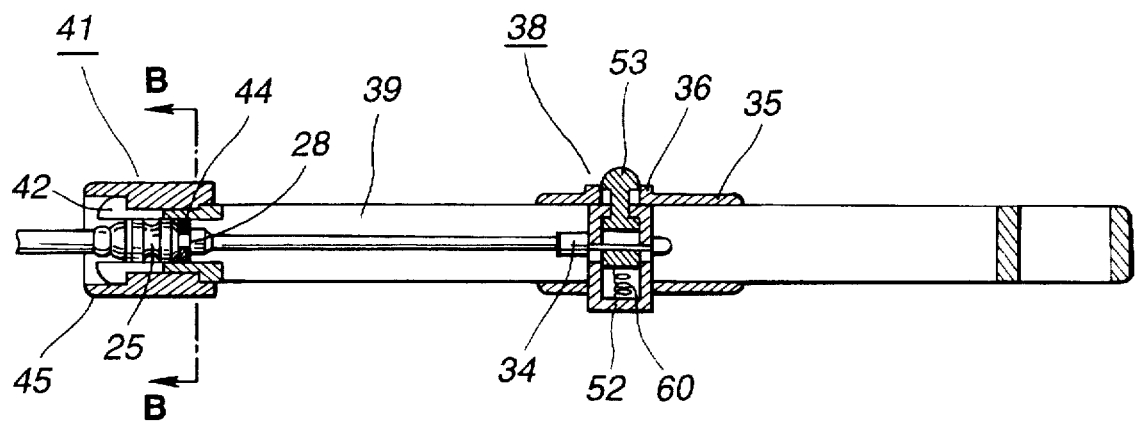

FIG. 13 is a sectional view showing the construction of the main body of the operating section of a treatment instrument.

Figure 14:
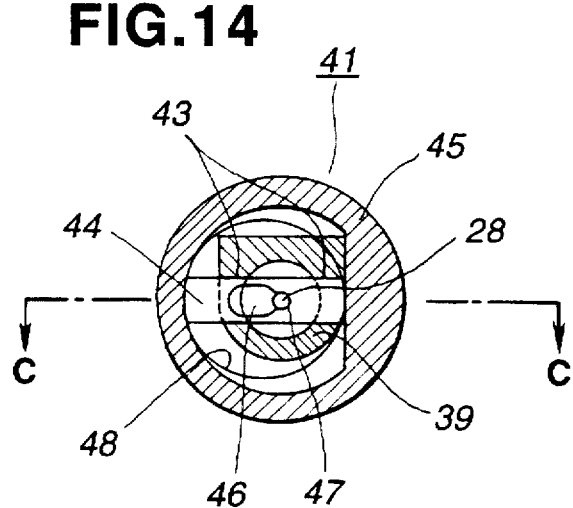
Figure 15:
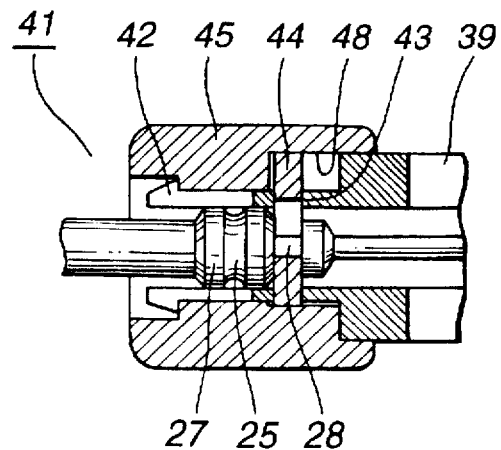
Figure 16:
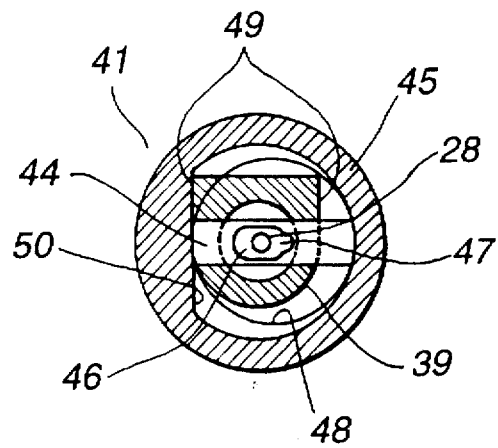

FIGS. 14–16 show the construction of the means for fixing the mouth metal of a flexible sheath.

FIG. 14 is a sectional view taken along the lines B—B in FIG. 13.

FIG. 15 is a sectional view taken along the lines C—C in FIG. 14.

FIG. 16 is a sectional view taken along the lines B—B in FIG. 13.

Figure 17:
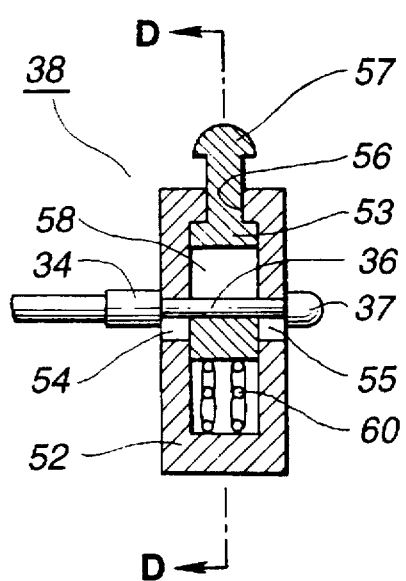
Figure 18:
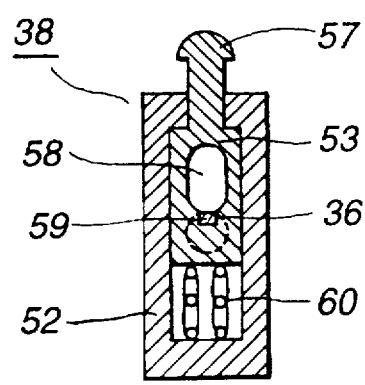

FIGS. 17 and 18 show the construction of the means for holding a fixing member to which the operating pipe is connected and FIG. 17 is an expanded sectional view of FIG. 13.

FIG. 18 is a sectional view taken along the lines D—D.

Figure 19:
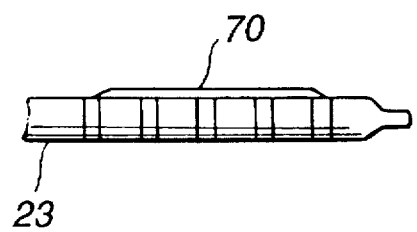

FIG. 19 is an explanatory drawing showing the construction of the front end of a treatment instrument related to the tenth embodiment.

Figure 20:
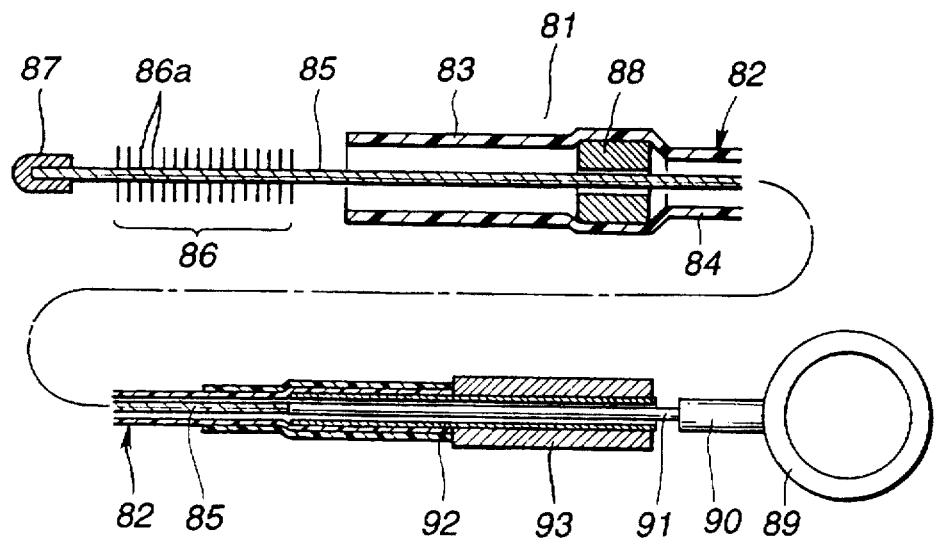

FIG. 20 is a sectional view showing the entire construction of the treatment instrument related to the eleventh embodiment.

Figure 21:
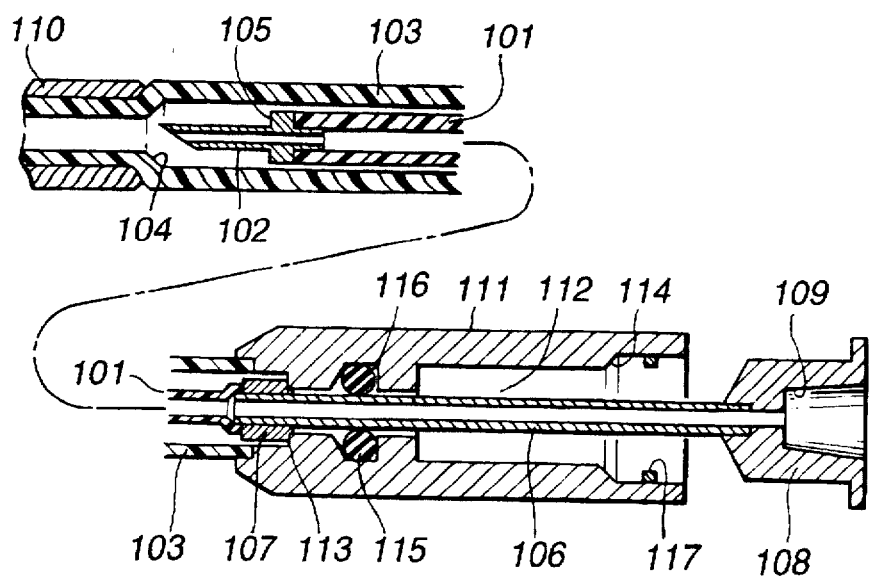

FIG. 21 is a sectional view showing the construction of a device for injecting fluid to the body which is a disposable medical instrument related to the twelfth embodiment.

Figure 22:
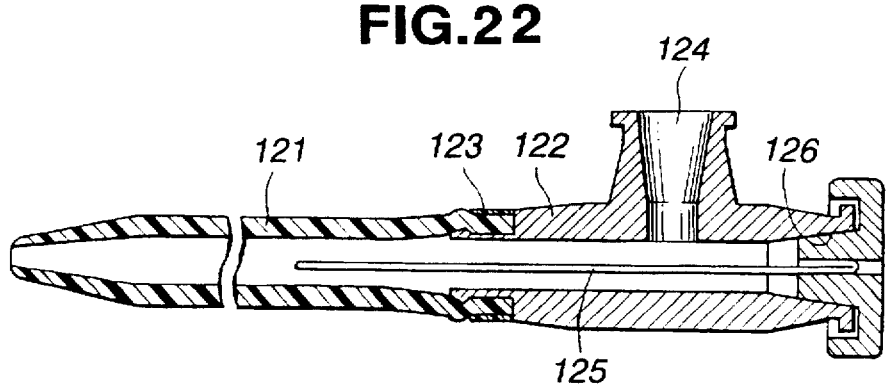

FIG. 22 is a sectional view showing the construction of an endoscope treatment instrument related to the thirteenth embodiment.

DETAILED DESCRIPTION OF THE PREFERRED EMBODIMENTS

FIGS. 1–8 show the first embodiment of the present invention.

The present embodiment will be described regarding disposable medical instruments which are used for biopsy or excision.

Figure 1:
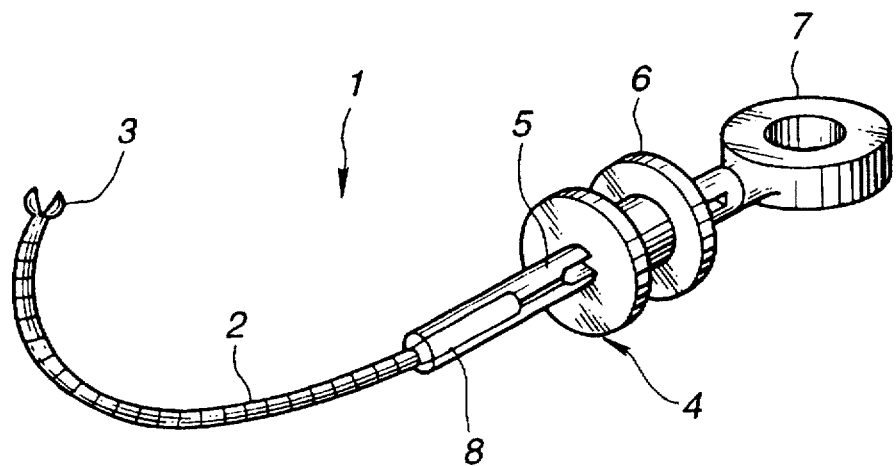
FIGS. 1–8 are related to the first embodiment of the present invention and FIG. 1 is a perspective view showing the entire construction of a disposable medical instrument.

As shown in FIG. 1, a medical instrument 1 comprises a sheath 2 which is long, narrow and flexible, a treatment section 3 which is provided at the front end of the sheath and an operating section 4 which is provided at the rear end of the sheath 2. An advancing/retracting member which is composed of a wire or the like (not shown) is inserted through the sheath 2. The front end of the advancing/retracting member is connected to the treatment section 3 and the rear end thereof is connected to the operating section 4. When the operating section 4 is operated, movements of the operating section 4 are transmitted to the treatment section 3 via the advancing/retracting member in order to operate a treatment member, such as a clamp for biopsy, which is provided at the treatment section 3.

The operating section 4 does not directly contact the mucosa of body cavities and an operating section main body 5. A slider 6 is disposed in the center of the operating section main body 5 so that the slider 6 is slidable along the circumference of the operating section main body 5. The advancing/retracting member is connected to the slider 6 so as to push or pull the advancing/retracting member. A finger ring 7 over which the finger is hooked to advance or retract the slider 6 is provided at the rear end of the operating section main body 5. A fixing plate which is engaged in the operating section main body 5 to fix the sheath 2 is provided at the front portion of the operating section main body 5.

Figure 2:
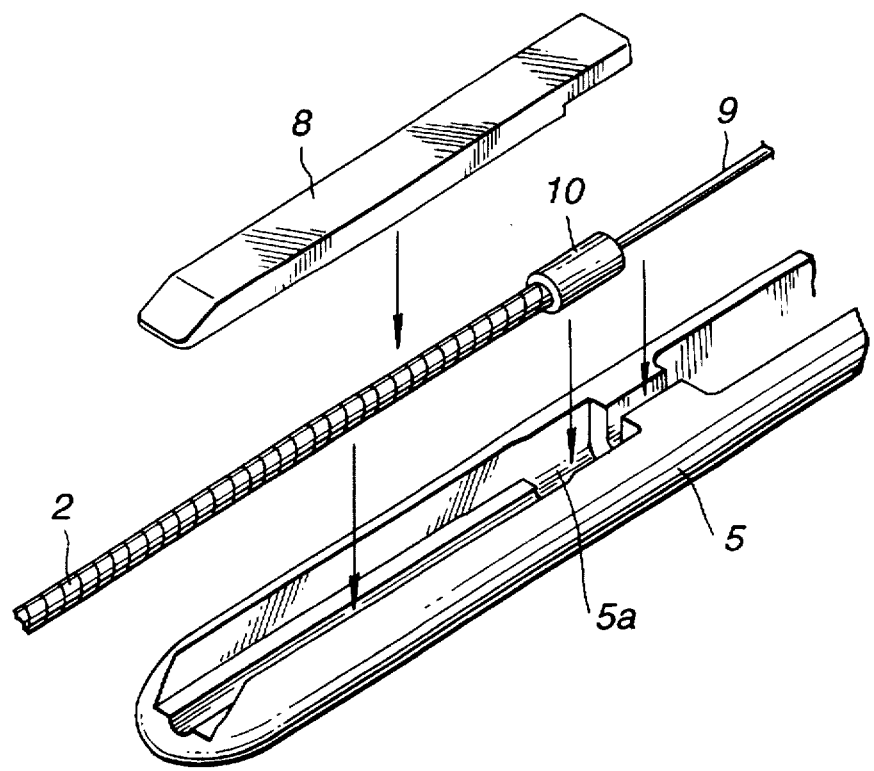

FIGS. 2–4 show the construction of the front portion of the operating section main body 5.

Within the sheath 2, the aforementioned advancing/retracting member 9 extends up to the operating section main body 5. A stopper ring 10 is fixed at the rear end of the sheath 2 by caulking or the like. The rear end of the sheath 2 containing the stopper ring 10 is inserted into a concavity 5a in the operating section main body 5 and the fixing plate 8 is pressed into and engaged in the operating section main body 5 to fix the rear end of the sheath 2 in the operating section main body 5 as shown in FIG. 4. The fixing plate 8 is made of water soluble polymer which is a hydrophilic material.

FIGS. 5 and 6 show the construction near the slider 6 in the center of the operating section main body 5.

A pressing plate 11 for fixing the end of the advancing/retracting member 9 to the slider 6 is provided between the operating section main body 5 and the slider 6 so as to engage with the slider 6. As shown in FIG. 6, the pressing plate 11 has a concavity 11a in which a stopper member 12 disposed at the rear end of the advancing/retracting member 9 is engaged at one end and has pawls 11b which lock on the edge of the slider 6 at the other end.

With the stopper member 12 of the advancing/retracting member 9 incorporated in the concavity 11a, the pressing plate 11 is inserted into the slider 6, and as shown in FIG. 5, the concavity 11a is elastically deformed maintaining the stopper member 12. The pawl 11b is locked on the slider 6 so as to fasten the pressing plate 11. Consequently, the rear end of the advancing/retracting member is fixed to the slider 6 so that the advancing/retracting member 9 can be advanced or retracted by sliding the slider 6 with respect to the operating section main body 5.

FIGS. 7 and 8 show the construction of the rear of the operating section main body 5.

The rear end of the operating section main body 5 has a protrusion 5b which engages with the finger ring 7 as shown in FIG. 7, and the protrusion 5b is inserted in to the engagement portion of the finger ring 7 and then engaged therewith. As a result, as shown in FIG. 8, the finger ring 7 is connected to the rear end of the operating section main body 5.

When a treatment instrument having the construction described above is used, the treatment section 3 is inserted into a treatment location of body cavities. With the thumb inserted into the finger ring 7, the slider 6 is moved back and forth with the forefinger and the middle finger. Consequently, the advancing/retracting member 9 which extends through the sheath 2 is pushed or pulled to operate the treatment section 3, thereby achieving a desired medical treatment.

The treatment instrument according to the present embodiment is disposable so that it is thrown away after use, prohibiting reuse. However, there are some operators who reuse used instruments. In this case, used instruments are cleaned with water or chemical fluid, disinfected or sterilized after use. If the treatment instrument according to the present embodiment is washed in water for reuse after use, the fixing plate which is a fixing member made of water soluble polymer is dissolved in water so that the sheath 2 is removed from the operating section main body 5, making it impossible to reuse the treatment instrument.

According to the present embodiment, because part of the components is dissolved if a used treatment instrument is washed in water, reuse of the disposable instrument is prohibited, preventing reuse of the instrument.

According to the second embodiment, the fixing plate 8 according to the first embodiment is made of ordinary plastic and instead the pressing plate for fixing the end of the advancing/retracting member 9 to the slider 6 is composed of water soluble polymer.

When a treatment instrument is constructed as described above, if the treatment instrument is washed in water after use, the pressing plate 11 composed of water soluble polymer which functions as a movable fixing part is dissolved in water, and thus, even if the slider 6 is slid, a force applied to the slider 6 is not transmitted to the advancing/retracting member 9 so that it is impossible to advance or retract the advancing/retracting member 9.

Thus, like the first embodiment, it is impossible to disable the reuse of a disposable medical instrument in order to prevent it from being reused.

According to the third embodiment, the fixing plate 8 according to the first embodiment is made of polymeric material (including elastomer) such as plastic containing more than 50% water soluble polymer (weight ratio).

According to the construction above, it is not only possible to disable the reuse of a disposable medical instrument as in the first embodiment but also it is possible to enhance the fixing strength of the components for ordinary use (before washing in water). Further, by changing the water soluble polymer content ratio, it is possible to control the fixing strength of the aforementioned components and the speed of fixing plate 8's dissolving in water when the medical instrument is washed in water.

According to the fourth embodiment, the fixing plate 8 according to the first embodiment is made of ordinary plastic and the pressing plate 11 is composed of polymeric material (including elastomer) such as plastic which contains more than 50% water soluble polymer (weight ratio).

If the treatment instrument is constructed as described above, it is not only possible to enhance the fixing strength of the components for ordinary use as in the third embodiment, but also by changing the water soluble polymer content ratio, it is possible to control the fixing strength of the aforementioned components and the speed of pressing plate 11's dissolved in water when the treatment instrument is washed in water.

According to the fifth embodiment, the fixing plate 8 or the pressing plate 11 according to the first embodiment is composed of water absorptive polymer which is a hydrophilic material.

When the treatment instrument is constructed as described above, if a used instrument is washed in water for reuse, the fixing plate 8 or the pressing plate 11 which is made of water absorptive polymer absorbs water so that it expands or softens. As a result, the fixing plate 8 or the pressing plate 11 becomes loose or the pressing plate 11 sticks to the operating section main body 5 so that the slider 6 cannot be moved, prohibiting reuse.

Thus, if the treatment instrument is washed in water after use, part of the components expands or softens so as to be inactivated. Thus, it is possible to prevent a disposable medical instrument from being reused like the first embodiment.

According to the sixth embodiment, the fixing plate 8 or the pressing plate 11 according to the first embodiment is composed of polymeric material (including elastomer) such as plastic which contains more than 20% water absorptive polymer (weight ratio).

When the treatment instrument is constructed as described above, it is not only possible to disable the reuse of the disposable medical instrument as in the fifth embodiment, but also by changing the water absorptive polymer content ratio, it is possible to control the fixing strength of the components for ordinary use and the speed of the water absorption of the fixing plate 8 or the pressing plate 11 when the instrument is washed in water.

If movable members or members for fixing other members of the medical instrument are composed of a material containing hydrophilic polymer as in the embodiments described above, the instrument's function is inactivated or the construction is destroyed when the used instrument is reused, thereby preventing reuse.

FIG. 9 is a sectional view showing the construction near the slider which is provided in the center of a treatment instrument according to the seventh embodiment.

A treatment instrument according to the seventh embodiment has a marking member 14 for indicating that the instrument has been washed, the marking member being provided in the slider 13 provided in the operating section 4. The marking member 14 is made of a material containing hydrophilic polymer mentioned in the first–sixth embodiments. The other construction is the same as that of the first embodiment.

If the treatment instrument having the above construction is washed in water for reuse after use, the marking member 14 is dissolved in water or absorbs water to expand. For this reason, according to the seventh embodiment, an operator can judge easily whether the treatment instrument has been already used and then washed depending on the condition of the marking member 14.

FIGS. 10 and 11 show the eighth embodiment of the present invention.

According to the eighth embodiment, in the concavity of the operating section main body 5 in which the sheath 2 is locked, a water absorptive ring 15 which acts as a movable stopper member is disposed behind the stopper ring 10 at the rear end of the sheath 2 and the advancing/retracting member 9 extends through the water absorptive ring 15. The water absorptive ring 15 is composed of water absorptive polymer or a material containing water absorptive polymer such as plastic, so that when water enters, the ring 15 absorbs water and expands. The fixing plate 8 is composed of ordinary plastic and the other construction is the same as that of the first embodiment.

If the treatment instrument having the construction described above is washed in water for reuse after use, as shown in FIG. 11, the water absorptive ring 15 expands so that the advancing/retracting member 9 is seized by the water absorptive ring 15, prohibiting the movement of the advancing/retracting member 9.

Thus, according to the present invention also, if the treatment instrument is washed in water after use, the water absorptive ring 15 expands so that the advancing/retracting member 9 is inactivated. Thus, it is possible to disable reuse of the disposable medical instrument preventing it from being reused.

Although, in the embodiments described above, the fixing plate 8 and the pressing plate 11 are made of a material containing hydrophilic polymer, the embodiments are not restricted to these cases and it is permissible to construct the components which do not directly contact the mucosa in body cavities, such as the finger ring 7 and the operating section main body 5, of the aforementioned material.

FIGS. 12–18 show the ninth embodiment of the present invention.

The ninth embodiment shows an example of the construction of a high-frequency excision tool which is an example of the disposable medical instruments.

As shown in FIG. 12, the high-frequency excision tool comprises an insertion section 21 which is inserted through the introducing channel of an endoscope and an operating section main body 22 which is attachable to the rear end of the insertion section 21.

The insertion section 21 comprises a flexible sheath 23 which is composed of an insulating material and an electric conductive wire 24 which is introduced through the flexible sheath 23 forming a treatment electrode.

A mouthpiece 25 which is formed of water soluble polymer is connected to the rear end of the flexible sheath. To prevent the flexible sheath 23 from being bent, a bend preventing tube 26 which is connected to the mouthpiece 25 is mounted on the flexible sheath 23. A large-diameter portion 27 is formed in the center of the mouthpiece and a protrusion 29 having a diameter intermediate between the large-diameter portion 27 and the indented portion 28 is formed behind the large-diameter portion 27 with the small-diameter indented portion 28 interposed therebetween. A through hole 30 is provided in the mouthpiece along the axis thereof. The electric conductive wire 24 to be inserted through the flexible sheath 23 has a snare 31 which is a loop-like treatment electrode provided at the end of the electric conductive wire.

An operating pipe 33 through which the electric conductive wire 24 is inserted is fixed at the rear end of the electric conductive wire 24. The operating pipe 33 is fixed to the fixing member 34 together with the electric conductive wire 24 so that the operating pipe 33 protrudes out of the through hole 30 of the mouthpiece 25. The fixing member 34 has an indented portion 36 having a small square cross section which is formed in the center along the axis of the fixing member 34 so as to be connected to the control member 35 and a protrusion 37 having a diameter larger than the indented portion 36 is formed at the end of the fixing member 34. Then, the fixing member 34 is fixed to a holding means 38 of the control member 35 of the operating section main body 22 as described later.

The operating section main body 22 has a finger ring 40 which is connected to a pair of bars 39. As shown in FIGS. 13–16, the end of the bars 39 has a mounting means 41 which includes a chuck 42 having four division slots, a sliding piece 44 which is slidably inserted in a slit 43 provided behind the chuck 42 and a rotating ring 45 which is engaged with the chuck 42 so that it can rotate around the chuck 42. Near the center of the sliding piece 44, a large-diameter hole 46 having a diameter allowing the fixing member 34 and the protrusion 29 of the mouthpiece 25 to be inserted therethrough and a small-diameter hole 47 having almost the same diameter as that of the indented portion 28 of the mouthpiece 25 are made so that they are in a continuous state. Inside the rotating ring 45, a cam circumferential surface 48 of a circular shape is formed so as to be deviated from the center axis of the rotating ring 45. The diameter of the cam circumferential surface 48 is the same as the longitudinal length of the sliding piece 44. At the rear end of the cam circumferential surface 48, a contacting surface 50 which restricts the rotation of the rotating ring 45 by contacting a flat portion 49 of the bar 39 is provided.

With the construction described above, if the rotating ring 45 is rotated until the contacting surface 50 of the rotating ring 45 contacts the plate portion 49 of the bar 39, the sliding piece 44 slides along the cam circumferential surface 48 as shown in FIGS. 14 and 16. By this rotation, the mouthpiece 25 is fit to or removed from the mounting means 41.

A pair of finger rings 51 are provided on the control member 35 which slides on a pair of the bars 39 of the operating section main body 22 and a holding means 38 for holding the fixing member 34 is provided in the center of the control member 35. The holding means 38 comprises a cylinder 52 and a piston 53.

As shown by an expanded sectional view of FIG. 17, the cylinder 52 has introducing holes 54, 55 through which the protrusion 37 of the fixing member 34 can be introduced along the length of the operating section main body 22. Further, a hole 56 which allows the head of the piston 53 to slide therethrough is made at the top portion of the cylinder 52. The piston 53 has a control button 57 which is formed so as to protrude from the cylinder 52. As shown in FIG. 18, an insertion hole 58 through which the protrusion 37 of the fixing member 34 can be inserted is made in the center of the piston 53 within the cylinder 52 and a square groove 59 which engages with the indented portion 36 of the fixing member 34 having a square cross section is formed at the bottom of the insertion hole 58, preventing the fixing member 34 from being rotated with respect to the indented portion 36. The piston 53 is urged upward by a coil spring 60 provided within the cylinder 52 so that a gap communicating the introducing holes 54, 55 with the insertion hole 58 of the piston 53 is smaller than the width of the indented portion 36 of the fixing member 34.

With the construction described above, the fixing member 34 is attached or detached by pressing down the control button to resist the urging of the coil spring 60 to make the introducing holes 54, 55 of the cylinder 52 coincide with the insertion hole 58 of the piston 53.

When the high frequency excision tool having the construction described above is used, the control member 35 of the operating section main body 22 is slid to operator's side to pull the loop-like snare 31 which acts as a treatment electrode into the flexible sheath. With this condition, the insertion section 21 of the high frequency excision tool is inserted into body cavities in the same manner as endoscopes, the front end of the flexible sheath 23 is located at a object location. Then, by sliding the control member 35 toward the front end, the snare 31 is protruded from the flexible sheath 23. The snare 31 is hooked over a polyp (not shown) in body cavities and then the control member 35 is slid to the operator's side in order to strangle the polyp by means of the snare 31. After this, high frequency current is fed to the electric conductive wire 24 to cut off the polyp. If the high frequency excision tool according to the present embodiment is washed for reuse after use, the mouthpiece 25 which is composed of water soluble polymer and is a fixed member which engages with the sliding piece 44 is dissolved in water so that the hooking of the sliding piece 44 is eliminated making it impossible to use the tool.

In the present embodiment also, if a used treatment instrument is washed, part of the components is dissolved in water. Thus, it is possible to disable reuse of the disposable medical instrument preventing reuse of the instrument.

Although, according to the present embodiment, the mouthpiece is composed of water soluble polymer, it is permissible to construct the mouthpiece of other materials containing hydrophilic polymer as indicated in the embodiments described above. Also, it is permissible to construct other components using the aforementioned material if it can be indicated whether the instrument cannot be reused or have been already used.

FIG. 19 is an explanatory drawing showing the construction of the front end of a treatment instrument related to the tenth embodiment.

In the tenth embodiment, a papillotomy knife is provided at the front end of the treatment instrument of the ninth embodiment. Instead of the snare 31, a wire knife 70 is provided along the side of the front end of the flexible sheath 23 of the insertion section of a treatment instrument. The other construction is the same as the ninth embodiment.

When the treatment instrument according to the present embodiment is used, the treatment instrument is inserted into body cavities as in the ninth embodiment and then the front end of the flexible sheath 23 is inserted into the duodenal papilla. Then, by sliding the control member 35 toward the operator's side to pull the wire knife, the front end of the flexible sheath 23 is curved. With this condition, high frequency current is fed to the wire knife 70 to cut off the duodenal papilla.

In the present embodiment also, if a used treatment instrument is washed for reuse, the mouthpiece 25 made of water soluble polymer is dissolved prohibiting reuse.

FIG. 20 is an explanatory drawing of the sectional view of the entire construction of a treatment instrument according to the eleventh embodiment.

According to the eleventh embodiment, a construction example of the cytologic brush tool is shown as an example of disposable medical instruments.

The cytologic brush tool 81 according to the present embodiment includes a sheath pipe 82 made of synthetic resin and the sheath pipe 82 contains a large-diameter portion 83 which is located at the front end and a small-diameter portion 84 which extends after the large-diameter portion toward the operator's side. The operating wire 85 runs through the sheath pipe 82. The operating wire 85 is composed of two stranded metallic wires and has a brush section 86 at the front end, which is constructed of a large number of short fibers 86a. The diameter of the brush section 86 is larger than the inside diameter of the sheath pipe 82 at the operator's side. Further, a front tip 87 is attached to the front end of the operating wire. The short fibers 86a of the brush section 86 are implanted securely in the operating wire and the wires of the brush section 86 are densely stranded to prevent the short fibers 86a from becoming loose.

A cylindrical limiting member 88 is fixed inside the rear end of the large-diameter portion 83 which is larger than the inside diameter of the front end of the small-diameter portion 84 of the sheath pipe 82 and an operating wire 85 runs through a hole in the center of the limiting member 88. A wire control member 90 having a finger ring 89 is connected to the rear end of the operating wire 85 through a connecting member 91. On the other hand, at the rear end of the sheath pipe 82, a holding member 93 is disposed with the fixing pipe 92 interposed and fixed around the circumference of the rear end of the fixing pipe 92. A connecting member 91 which is connected to the wire control member 90 having a finger ring is slidably inserted through the fixing pipe 92. In the cytologic brush 81, the finger ring 89 of the wire control member 90 is made of water soluble polymer.

When the cytologic brush tool 81 having the construction described above is used, with the thumb hooked over the finger ring 89, the operating wire 85 is pulled in by pulling the wire control member 90 to the operator's side in order to store the brush section 86 within the sheath pipe 82. After an endoscope is inserted into body cavities and the insertion section of the endoscope is introduced to an object location, the cytologic brush tool 81 is inserted through the endoscope channel.

When the front end of the sheath pipe 82 is led near organizations of an object location, the wire control member 90 having the finger ring 89 is pushed forward, the operating wire 85 advances through the sheath pipe 82 through the fixing pipe 92 and as shown in FIG. 20, the brush section 86 protrudes from the front end of the sheath pipe 82. By moving the wire control member 90 back and forth with respect to the sheath pipe 82, the brush section 86 brushes organizations on the internal wall of body cavities so that cells of the organization adhere to the brush section 86. After this, by pulling the wire control member 90 to the operator's side, the brush section 86 is pulled into the sheath pipe 82 until it contacts the limiting member 88 provided within the large-diameter portion 83 of the sheath pipe 82 and with this condition, the cytologic brush tool 81 is pulled out of body cavities through the endoscope channel. Consequently, it is possible to obtain cells of the organizations of the object location.

In the present embodiment also, if a used cytologic brush tool is washed for reuse, the finger ring 89 which is a grip member made of water soluble polymer is dissolved prohibiting reuse of the tool.

Although the finger ring 89 is composed of water soluble polymer in the present embodiment, it is permissible to construct the cytologic brush tool using the other hydrophilic water soluble polymer shown in the above embodiments. Additionally, it is also permissible to construct the other components using the aforementioned material if it is indicated whether the tool cannot be reused or has been already used.

FIG. 21 is an explanatory drawing showing the construction of a device for injecting fluid to the body which is a disposable medical instrument related to the twelfth embodiment.

The twelfth embodiment shows an example of the construction of the device for injecting fluid to the body which is a disposable medical instrument.

In the device for injecting fluid to the body according to the present embodiment, a tubular tip needle 102 is fixed at the front end of a flexible injecting tube 101 formed of transparent synthetic resin such as PTFE. The front portion of the tip needle is formed so that the outside diameter is smaller than that of the injection tube 101 except the rear end. In the edge of the rear end of the tip needle 102, a contacting surface 105 is formed so that it locks in the contacting portion of the sheath pipe 103 as described later.

A metallic pipe 106 having the same diameter as the injecting tube 101 is connected to the rear end of the injecting tube 101. A ring-like stopper 107 is fit to this connecting portion to prevent the injecting tube 101 from becoming loose. A mouth metal 108 is connected to the rear end of the metallic pipe 106. In the mouth metal 108, a connecting mouth 109 to which an injector (not shown) such as a syringe is connected is formed. The injecting tube 101 and the tip needle 102 are inserted through the sheath pipe 103 which is a flexible pipe made of transparent synthetic resin such as PTFE so that they are slidable back and forth.

At the front end of the sheath pipe 103, the contacting portion 104 the inside diameter of which is slightly larger than the outside diameter of the tip needle 102 is provided. The contacting surface 105 of the tip needle 102 contacts the contacting portion 104 to limit the protrusion of the tip needle 102. A restricting member 110 made of a metallic pipe the inside diameter of which is smaller than the outside diameter of the sheath pipe 103 is adhered to the circumference at the front end of the sheath pipe 103. A cylindrical holder 111 is fixed to the rear end of the sheath pipe 103. A passage hole 112 is made in the holder 111 and the metallic pipe 106 runs through the passage hole 112. At the front end of the passage hole 112, a first locking portion 113 is formed so that the stopper 107 prevents the injecting tube from becoming loose. At the rear end of the passage hole 112, a second locking section 114 is formed so that the front end of the mouth metal 108 locks therein to prevent the injecting tube 101 from entering into the passage hole 112.

When the contacting surface 105 of the tip needle 102 locks in the contacting portion 104 after the injecting tube 101 is advanced, the mouth metal 108 locks in the second locking portion 114. Therefore, when the mouth metal 108 is pushed up to the second locking portion 114, the injecting tube 101 is elastically compressed, so that the tip needle 102 is kept protruding from the sheath pipe 103 by means of a restoring force of the injecting tube 101. A groove holding an O-ring like elastic object 115 which contacts the metallic pipe 106 is formed in the midway of the holder 111. On the inside surface of the passage hole at the rear end, a protrusion 117 is provided so that it contacts the circumference of the mouth metal 108 elastically to keep the mouth metal 108 pressed in. The protrusion 117 is formed of water soluble polymer.

When the aforementioned device for injecting fluid to the body is used, the tip needle 102 is inserted through the sheath pipe preliminarily, then the sheath pipe 103 is inserted through the endoscope instrument channel (not shown) and the device is protruded into body cavities. After the front end of the sheath pipe 103 is introduced near an object location, the mouth metal 108 on the operator's side is pushed until the contacting surface of the tip needle 102 which is advanced through the injecting tube 101 contacts the contacting portion 104 of the sheath pipe 103. Consequently, the tip needle 102 protrudes at its specified length.

If the mouth metal 108 is further pressed in, the injecting tube 101 is elastically compressed within the sheath pipe and at the same time, the circumference of the mouth metal 108 elastically locks in the protrusion 117 of the locking portion 114 preventing the mouth metal 108 from retracting. Thus the protrusion of the tip needle 102 is maintained with good condition. An object location is pricked with the tip needle 102 and chemical fluid is injected through the injecting tube 101 from an injector (not shown) which is connected to the connecting mouth 109 of the mouth metal 108.

In the present embodiment also, if a used device is reused, the protrusion 117 which is made of water soluble polymer, acting as a fixing member, is dissolved so that the mouth metal 108 cannot lock in the second locking portion 114 making it possible to disable reuse. Consequently, it is possible to prevent reuse of a disposable medical instrument.

Although, in the present embodiment, the protrusion 117 is composed of water soluble polymer, it is permissible to construct the protrusion using the other hydrophilic polymers shown in the above embodiments. Also it is permissible to construct the other components using the aforementioned materials if it is indicated whether the device cannot be reused or has been already used.

FIG. 22 is a sectional view showing the construction of the endoscope treatment instrument related to the thirteenth embodiment.

The thirteenth embodiment shows an example of the construction of an imaging tube device which is an endoscope treatment instrument as an example of the disposable medical instrument.

The imaging tube device according to the present embodiment contains a flexible sheath 121 formed of a flexible material such as PTFE, the flexible sheath 121 being inserted through the endoscope treatment instrument introducing channel. At the rear end of the flexible sheath 121, an operating section 122 is pressed into the flexible sheath 121 and then fixed by a stopper ring 123 made of water soluble polymer.

A first mouth metal 124 to which a syringe for supplying chemical fluid is fit is provided above the aforementioned operating section and a second mouth metal 126 for engaging a buckle preventing wire 125 is provided on the operator's side. The buckle preventing wire 125 is inserted up to the midway of the flexible sheath 121 through the second mouth metal 126.

When the imaging tube device having the construction described above is used, the flexible sheath 121 is inserted into body cavities through the endoscope, a syringe containing chemical fluid is fit to the first mouth metal 124 and the chemical fluid is supplied to body cavities from the syringe through the flexible sheath 121.

In the present embodiment also, if a used device is washed for reuse, the stopper ring 123 which is made of water soluble polymer, acting as a fixing member is dissolved so that the flexible sheath becomes likely to become loose from the operating section 122. Thus it is possible to disable reuse of the device.

Although, in the present embodiment, the stopper ring 123 is composed of water soluble polymer, it is permissible to construct the ring using the other hydrophilic polymers shown in the above embodiments. Also it is permissible to construct the other components using the aforementioned materials if it is indicated whether the device cannot be reused or has been already used.

Meantime, it is possible to apply the present invention to other disposable medical instruments as well as the treatment instruments described in the respective embodiments.

As described above, according to the present invention, it is possible to disable reuse if a device according to respective embodiments is washed or judge easily whether a used device is washed for reuse, preventing reuse of a used device.

According to the present invention, it is evident that different embodiments can be constructed in a wide range without deviating from the spirit and the scope of the invention. The present invention is not restricted to specific embodiments except that it is restricted by the accompanying claims.

What is claimed is:

1. A disposable medical instrument comprising:

a treatment section comprising non-degradable material at a front end of the instrument capable of performing a treatment of body cavities;

a flexible sheath comprising non-degradable material extending from said treatment section at the front end to an operator side of the instrument; and an operating section provided at the operator side of said sheath, said operating section not directly contacting mucosa of body cavities, at least a part of the operating section being composed of a degradable material containing hydrophilic polymer, wherein said part of said operating section is arranged at a position which would contact with water when washed to thereby degrade said part of the operating section.

2. A disposable medical instrument according to claim 1, wherein said hydrophilic polymer is a water soluble polymer, so that said part of the operating section is dissolved when washed in water.

3. A disposable medical instrument according to claim 1, wherein the hydrophilic polymer is a water absorptive polymer, so that said part of the operating section absorbs water so as to expand or soften when washed in water.

4. A disposable medical instrument according to claim 2, wherein said part of the operating section is composed of a polymeric material containing 50% or more water soluble polymer at weight ratio.

5. A disposable medical instrument according to claim 3, wherein said part of the operating section is composed of a polymeric material containing 20% or more water absorptive polymer at weight ratio.

6. A disposable medical instrument according to claim 1, wherein said part of the operating section is at least one of a movable member, a gripping member, a fixing member for fixing a component and a fixed member which is fixed by engagement with a fixing member and is composed of a material containing hydrophilic polymer.

7. A disposable medical instrument according to claim 1, wherein said part of the operating section is the one comprising a marking member composed of a material containing hydrophilic polymer making it possible to judge whether said medical instrument has been washed.

8. A disposable medical instrument according to claim 3, wherein said part of the operating section is provided with a movement limiting member composed of a material containing water absorptive polymer, said movement limiting member being provided near a movable member in said medical instrument to limit movement of said movable member.

9. A disposable medical instrument according to claim 1, comprising a high frequency excision tool which has a treatment electrode at the front end in order to excise an affected part by supplying high frequency current to said treatment electrode.

10. A disposable medical instrument according to claim 1, comprising a cytologic brush which has a brush section at the front end of said medical instrument to collect body cells by moving said brush.

11. A disposable medical instruction according to claim 1, comprising a device for injecting fluid into the body, said device having an injecting tube and a syringe to supply said fluid by means of said injecting tube.

12. A disposable medical instrument according to claim 1, comprising an imaging tube device which has a flexible sheath to feed chemical fluid through said flexible sheath.

* * * * *